United States Patent
Nakatani et al.

(10) Patent No.: US 6,559,290 B1
(45) Date of Patent: May 6, 2003

(54) METHOD FOR REMOVING A CHEMOKINE

(75) Inventors: Masaru Nakatani, Kobe (JP); Shigeo Furuyoshi, Kobe (JP); Satoshi Takata, Takasago (JP)

(73) Assignee: Kaneka Corporation, Osaka (JP)

( * ) Notice: Subject to any disclaimer, the term of this patent is extended or adjusted under 35 U.S.C. 154(b) by 804 days.

(21) Appl. No.: 08/819,630

(22) Filed: Mar. 17, 1997

(30) Foreign Application Priority Data

Mar. 18, 1996 (JP) ............................................. 8/061158
Mar. 27, 1996 (JP) ............................................. 8/072916

(51) Int. Cl.$^7$ ............................................. C07K 17/00
(52) U.S. Cl. ........................ 530/415; 210/650; 435/7.2; 435/4
(58) Field of Search ............................ 424/78.08, 462, 424/85.1, 85.2; 435/69.1, 69.5, 69.51, 69.52; 55/660.9; 210/263, 650; 530/415, 412

(56) References Cited

U.S. PATENT DOCUMENTS

| | | | | |
|---|---|---|---|---|
| 4,049,772 A | * | 9/1977 | Takada et al. .................. | 423/54 |
| 5,180,812 A | * | 1/1993 | Dower et al. ................. | 530/351 |
| 5,216,127 A | * | 6/1993 | Hirai et al. ................... | 530/380 |
| 5,258,503 A | * | 11/1993 | Yokohari et al. ............ | 530/415 |
| 5,338,834 A | | 8/1994 | Williams ..................... | 530/351 |
| 5,403,917 A | * | 4/1995 | Boos et al. ................... | 530/351 |
| 5,437,861 A | * | 8/1995 | Okarma et al. ........... | 424/78.08 |
| 5,545,328 A | * | 8/1996 | Pliura et al. ................. | 210/635 |
| 5,707,815 A | * | 1/1998 | Charo et al. .................. | 435/7.2 |
| 5,804,370 A | * | 9/1998 | Romaschin et al. ............ | 435/5 |
| 6,203,997 B1 | * | 3/2001 | Romaaschin et al. ........ | 435/7.2 |

FOREIGN PATENT DOCUMENTS

| | | |
|---|---|---|
| EP | 0 592 989 A2 | 4/1994 |
| EP | 0 729 784 A1 * | 9/1995 |
| EP | 0 723 794 A1 | 7/1996 |
| EP | 0 729 784 A1 | 9/1996 |
| JP | 6-312017 | 11/1994 |
| JP | 7-101991 | 4/1995 |
| WO | WO 96/20042 | 12/1995 |
| WO | 96 20042 A | 7/1996 |
| WO | 96/20042 * | 7/1996 |

OTHER PUBLICATIONS

"Affinity of Dextran Sulfate–Cellulose Bead (DSCB) for Humoral Substances" Soeda, K. et al., 18(1), 331–334 (1989) w/partial English translation.
Immunology Today, vol. 15, No. 3: pp. 127–133 (1994).
Clinical Immunology, 27 [Suppl. 16]: pp. 162–171 (1995) with partial English Translation.
Clinical Immunology, 27 [Suppl. 16]: pp. 147–154 (1995) with partial English Translation.
Nature, vol. 365, 654–657 (1993).
Intensive & Critical Care Medicine, vol. 4; No. 12, pp. 1356–1365 (1992) with partial English Translation.
Nephrol Dial Transplant 10: 2077–2082 (1995).
Menekiyakuri, 12, No. 1, 15–21 (1994) with partial English Translation.
The Cytokine Data Manual, Nankodo, 105–108 (1995) with partial English Translation.
Intensive & Critical Care Medicine, 6(2), 105–114 (1994) with partial English Translation.
Intensive & Critical Care Medicine, 6(2), 115–123 (1994) with partial English Translation.

* cited by examiner

*Primary Examiner*—Jose' G. Dees
(74) *Attorney, Agent, or Firm*—Armstrong, Westerman & Hattori, LLP

(57) ABSTRACT

An adsorbent for removing a chemokine except interleukin-8 in body fluid, which comprises a solid material having an anionic functional group, a method for efficiently removing a chemokine except interleukin-8 in body fluid, which comprises by bringing the above adsorbent into contact with body fluid containing the chemokine and an adsorber for removing a chemokine except for interleukin-8 using the above adsorbent.

4 Claims, 1 Drawing Sheet

METHOD FOR REMOVING A CHEMOKINE

BACKGROUND OF THE INVENTION

The present invention relates to an adsorbent for removing a chemokine in body fluid, a method for removing a chemokine in body fluid by means of the adsorbent, and an adsorber for removing a chemokine from body fluid.

An immunocompetent cell produces various kinds of active substances when causing immune response. One portion thereof is a proteinous substance called a cytokine and plays a greatly important role as a biophylactic factor which is closely related to various kinds of antigen-specific response and/or non-specific inflammatory response. Essentially, a cytokine is necessary and indispensable for maintaining biological homeostasis and is produced excessively in pathological conditions such as inflammation and the like, relating to the formation and the prolongation of inflammation and the like.

Among the cytokines, especially, ones having chemotaxis are generically named chemokines. Chemotaxis is also referred to as chemotropism, and means tropism caused by difference in concentration of a chemical entity. It is known that the substances referred to as chemokines form one family for their structural characteristics.

Chemokines are characterized in that they exist mainly as proteins having a molecular weight of from about 6,000 to about 10,000. Depending on kinds of chemokines, however, there exist chemokines which form dimers or tetramers in fluid, and chemokines having a molecular weight more than 10,000 because of O-glycosylation. Also, chemokines are classified into the following two subfamilies according to their structural characteristics. One is CXC subfamily, and the other is CC subfamily. As shown in the Review "CC CHEMOKINES IN ALLERGIC INFLAMMATION", Immunology Today, 15, 127–133, 1994 by M. Baggiolini et al., a chemokine has four cysteine residues (hereinafter a cysteine residue is referred to as C) in a position firmly conserved in its molecule. When such four Cs are referred to as C1, C2, C3 and C4 in that order from N-terminus, chemokines are classified into CXC subfamily wherein one optional amino acid (hereinafter referred to as X) exists between C1 and C2, and CC subfamily wherein no amino acid exists between C1 and C2. Further, it is shown that chemokines in each subfamily have relatively high homology in a sequence of amino acids other than Cs (e.g., the report by Chihara, Clinical Immunology, 27 [Suppl. 16], 162–171, 1995).

It has been thought that CXC subfamily acts mainly on a neutrophil among leukocytes, while CC subfamily acts mainly on a monocyte, an eosinophil, a basophil and a lymphocyte among leukocytes. Recently, however, it has been suggested that they exert their effects on various kinds of cells as well as the above-mentioned leukocytes. For instance, it is known that interleukin-8 (IL-8) shows physiological activities on a lymphocyte, a basophil, an eosinophil, an epidermal keratinocyte, a melanomatous cell, a fibroblast and an endothelial cell as well as a neutrophilic, although interleukin-8 is an interleukin having chemotaxis among interleukins and is a chemokine classified into CXC subfamily (Matsushima, Clinical Immunology, 27 [Suppl. 16], 147–154, 1995).

Further, it is known that, on e.g., a human monocyte, there exist not only receptors specific to each of monocyte chemoattractant protein-1 (hereinafter referred to as MCP-1) and macrophage inflammatory protein-1 (hereinafter referred to as MIP-1) which are chemokines classified into CC subfamily, but also a common receptor specific to three kinds of chemokines classified into CC subfamily, i.e., MCP-1, MIP-1 and RANTES, (Regulated upon Activation in Normal T cells Expressed and Secreted) (Matsushima, Clinical Immunology, 27 [Suppl. 16], 147–154, 1995). This finding suggests that there exist chemokines in one subfamily which exert the same phisiological activity through the same receptor.

Once a living body has stress or infection from the out side, inflammation is caused as a biophylactic response, and there arises infiltration of leukocytes into an inflammatory site. Such infiltration of leukocytes into an inflammatory site is caused by leukocyte chemotactic factor produced at the inflammatory site. It is known that a chemokine plays a role as a causative factor of the infiltration of leukocytes. In fact, it has been demonstrated that administration of an antibody against interleukin-8 (anti-IL-8-antibody) being one of chemokines blocks infiltration of neutrophilics at a inflammatory site and inhibits a disorder of organ accompanied with acute inflammation in a model of a rabbit with acute inflammation (Sekido et al., Nature, 365, 654–657, 1993).

Furthermore, recently it has been reported that a network of cytokines is activated by overproduction of various cytokines, and induction and activation of neutrophils are caused by overproduction of chemokines due to the activation of the network of cytokines, in pathological conditions included in a conception of systemic inflammatory response syndrome (SIRS) (Endo et al., Intensive & Critical Care Medicine, 4, 1357–1365, 1992). It is suggested that thereby systemic inflammatory response progresses, and shock, a tissue disorder and pluriorganic insufficiency are caused, and then death may come.

It is suggested that at a pathologic site of allergic inflammation, various inflammatory cells such as a lymphocyte and an eosinophil infiltrate according to action of chemokines such as RANTES, platelet factor-4 (hereinafter referred to as PF-4) and macrophage inflammatory protein-1α (hereinafter referred to as MIP-1α), as key substances.

Also, for instance, in case of carrying out blood extracorporeal circulation such as dialysis therapy, the possibility has been suggested that chemokines are overproduced by stimulation to an immunocompetent cell by means of contact with an artificial material, an irritant represented by microbial endotoxin in dialysis, various irritant factors existing in blood or tissue, and the like. For instance, in dialysis amyloidosis or carpal tunnel syndrome which is a complication accompanied with a long-term dialysis therapy, the possibility has been suggested that MCP-1 or MIP-1α is overproduced and relates to formation of pathological conditions (Inoue et al., Nephrology Dialysis Transplantation, 10, 2077–2082, 1995).

Further, an abnormally higher concentration of interleukin-8 being one of chemokines has been detected at an inflammatory site or in peripheral blood of patients with diseases such as gouty arthritis, psoriasis, contact dermatitis, idiopathic fibroid lung, adult respiratory distress syndrome, inflammatory bowel disease, immune angiitis, urinary tract infection cardiac infarction, asthma, respiratory tract infection, perinatal infectious disease and rejection in organ transplantation, than that of a normal human (Menekiyakuri, 12, No. 1, 15–21, 1994).

Also, there abnormally appear interleukin-8, RANTES, MCP-1, MIP-1α and macrophage inflammatory protein-1β (hereinafter referred to as MIP-1β) in rheumatoid arthritis (RA); MCP-1, MIP-1α and MIP-1β in crescentic glomerulonephritis; interleukin-8 and MCP-1 in chronic glomerular nephritis; and MCP-1 in lupus nephritis. It is suggested that the chemokines concern formation of pathological conditions of the above-mentioned diseases.

Until now, there is no report as to a method for removing such chemokines which have various functions in body fluid. There is disclosed only a method for purifying blood with an adsorbent for removing an endotoxin and/or a cytokine caused by the endotoxin, which comprises a porous carrier having a cationic functional group on the surface (Japanese Unexamined Patent Publication No. 312017/1994). However, there is described neither measurement of the cytokine nor adsorption of the cytokine in Example thereof.

It is also considered that inhibition of chemokine's action, so-called anti-chemokine therapy is applied by administering an antibody against the chemokine or a substance which inhibits binding of the chemokine to a receptor thereof. However, it is necessary to prepare and administer an antibody against each chemokine in order to inhibit such action by administration of the antibody or the like, because it is suggested that many kinds of chemokines abnormally appear in pathologic conditions accompanied with chronic inflammation such as the above-mentioned rheumatoid arthritis. Further, an antibody or the like to be administered must not exert bad influence upon a human body, and it is considered that development thereof requires long term and a great cost. Therefore, it is hard to say that such therapy is suitable one.

In order to solve the above problems, an object of the present invention is to provide an adsorbent which can efficiently adsorb and remove various chemokines present in body fluid.

A further object of the present invention is to provide a method for removing the chemokines by means of the above-mentioned adsorbent.

A still further object of the present invention is to provide an adsorber for removing the chemokines with the above-mentioned adsorbent.

These and the other objects of the present invention will become apparent from the following description.

SUMMARY OF THE INVENTION

By investigating literatures, it became clear hat there were many chemokines having at least 7 of isoelectric point, namely having a positive charge in a physiological condition, while there were several chemokines having less than 7 of isoelectric point, namely a negative charge in a physiological condition. As a result of the continuous effort of the present inventors with respect to an adsorbent having ability to efficiently adsorb and remove chemokines with various charges existing in body fluid, it has been found that a solid material having an anionic functional group, particularly a styrene-divinylbenzene copolymer having a sulfonic acid group, strongly adsorbes a chemokine regardless of the isoelectric point thereof, in case where the solid material is brought into contact with the chemokine. Consequently the present invention has been accomplished.

The present applicant has previously filed the patent applications concerning the adsorbent for removing interleukins, which comprises a solid material having an anionic functional group (Japanese Patent Application No. 226906/1994 (National Republication of PCT Application No. PCT/JP95/01859 (WO 96/09115)) and Japanese Patent Application No. 229298/1995 (Japanese Unexamined patent publication No. 281101/1996)). Therefore, among interleukins, interleukin-8 having chemotaxis, which is a chemokine classified into CXC subfamily and has 8.6 of the isoelectric point, is excepted from the chemokine of the present invention.

In accordance with the present invention, there is provided (1) an adsorbent for removing a chemokine except interleukin-8 in body fluid, which comprises a solid material having an anionic functional group.

Further, there is provided (2) the adsorbent of the above-mentioned item (1), wherein the anionic functional group comprises at least one kind of functional group selected from the group consisting of sulfuric ester group, sulfonic acid group, carboxyl group and phosphoric ester group.

Further, there is provided (3) the adsorbent of the above-mentioned item (1) or item (2), wherein the solid material having an anionic functional group is a solid material onto which a polyanionic compound having plural anionic functional groups in its molecule is immobilized.

Further, there is provided (4) the adsorbent of the above-mentioned item (3), wherein the polyanionic compound is a synthetic polyanionic compound and/or a synthetic acidic polysaccharide.

Further, there is provided (5) the adsorbent of the above-mentioned item (1), wherein the solid material having an anionic functional group is a styrene-divinylbenzene copolymer having a sulfonic acid group.

Further, there is provided (6) the adsorbent of the above-mentioned item (5), wherein ion-exchange capacity of the styrene-divinylbenzene copolymer having a sulfonic acid group is from 0.01 meq/ml to 5 meq/ml.

Further, there is provided (7) a method for removing a chemokine except interleukin-8, which comprises by bringing the adsorbent of the above-mentioned item (1) into contact with body fluid containing the chemokine.

Further, there is provided (8) the method of the above-mentioned item (7), wherein the adsorbent for removing the chemokine comprises a styrene-divinylbenzene copolymer having a sulfonic acid group.

Further, there is provided (9) the method of the above-mentioned item (8), wherein ion-exchange capacity of the styrene-divinylbenzene copolymer having a sulfonic acid group is from 0.01 meq/ml to 5 meq/ml.

Further, there is provided (10) the method of the above-mentioned item (8), wherein a vessel which has an inlet and an outlet for fluid contains the adsorbent for removing a chemokine in the vessel.

Further, there is provided (11) an adsorber for removing a chemokine except interleukin-8, wherein a vessel which has an inlet and an outlet for fluid and is equipped with a means to prevent the adsorbent of the above-mentioned item (1) from flowing to the outside of the vessel, is charged with the adsorbent of the above-mentioned item (1).

Further, there is provided (12) the adsorber of the above-mentioned item (11), wherein the adsorbent for removing the chemokine comprises a styrene-divinylbenzene copolymer having a sulfonic acid group.

A variety of chemokines except interleukin-8 existing in body fluid can be efficiently adsorbed and removed by means of an adsorbent according to the present invention, which comprises a solid material having an anionic functional group. The present invention can provide an effective method for suppressing the effect of chemokines in various diseases caused by the chemokines.

DETAILED DESCRIPTION

Figure 1:
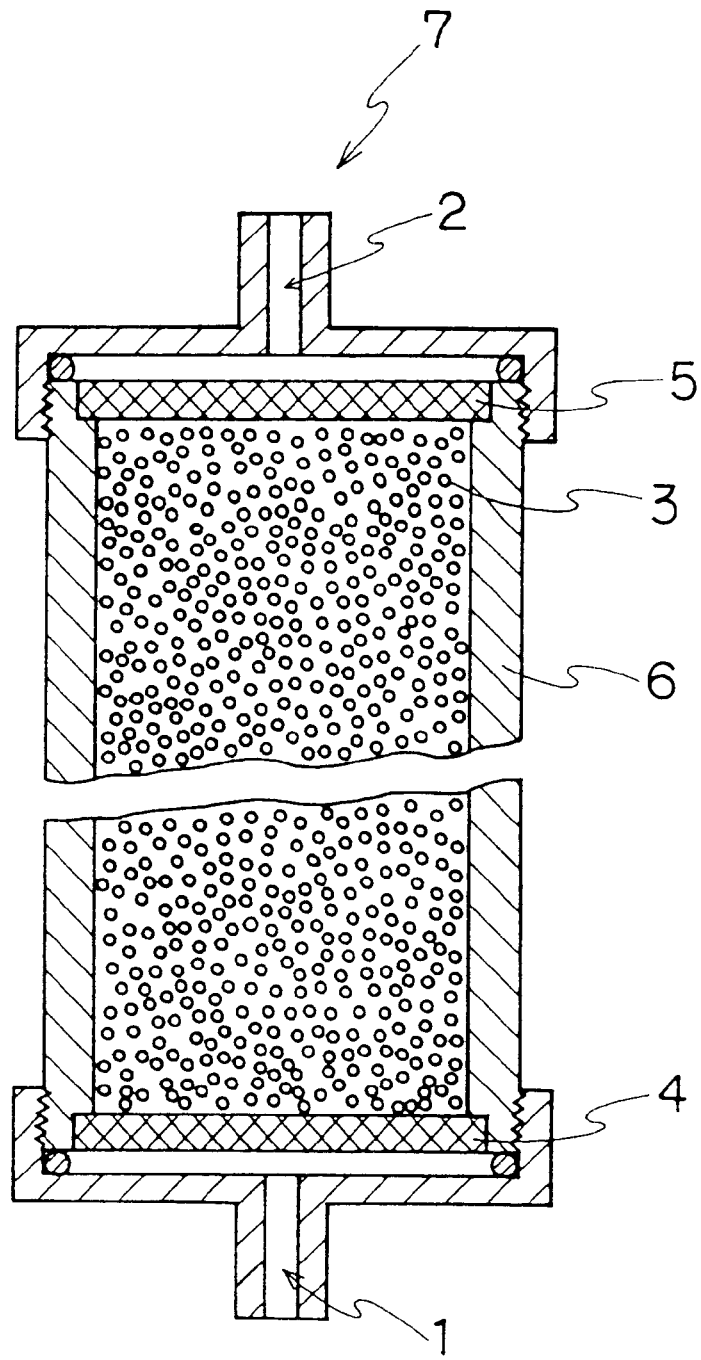
FIG. 1 is a schematic cross section of an Example of the adsorber for removing a chemokine of the present invention.

The term "body fluid" in the present invention means a liquid constituent derived from a living body such as blood, plasma, serum, ascites, lymph or synovia.

Also, the term "chemokine" in the present invention means a substance which has chemotaxis and is characterized in that there exist a gene coding for a chemokine that belongs to CXC subfamily in human chromosome 4 (q12–q21); and a gene coding for a chemokine that belongs to CC subfamily in human chromosome 17 (q11–q12). However, interleukin-8 is excepted from the chemokine in the present invention. Also, the chemokine of the present invention includes a substance being newly found in a future study and recognized to be in the category of the definition of the chemokine. Referring to Matsushima's report (Clinical Immunology, 27 [Suppl. 16], 147–154, 1995), Chihara's report (Clinical Immunology, 27, [Suppl. 16], 162–171, 1995) and the like, the following human chemokines known to date are exemplified. GRO$\alpha$, GRO$\beta$, GRO$\gamma$, neutrophil activating protein-2 (NAP-2), neutrophil activating protein-4 (NAP-4), epithelial-cell derived neutrophil-activating protein-78 (ENA-78), PF-4, interferon-inducible protein 10 (IP-10), granulocyte chemotactic protein-2 (GCP-2), $\beta$-thromboglobulin ($\beta$-TG) and pre-B cell growth stimulating factor (PBSF) are exemplified as chemokines classified into CXC subfamily, and MCP-1, HC14, monocyte chemoattractant protein-3 (MCP-3), I-309, MIP-1$\alpha$, MIP-1$\beta$, and RANTES are exemplified as chemokines classified into CC subfamily. However, since a name of a chemokine is not often unified, there is a case where one chemokine is referred to as a different name. For example, in the published book edited by Department of Microbiology, Kyoto Prefectural University of Medicine, "Cytokine Data Manual, Nankodo", 1995, there is described that GRO$\beta$ and GRO$\gamma$ are referred to as macrophage inflammatory protein-2$\alpha$ (MIP-2$\alpha$) and macrophage inflammatory protein-2$\beta$ (MIP-2$\beta$), respectively; and MCP-1 is referred to as monocyte chemotactic and activating factor (MCAF); and HC14 is referred to as monocyte chemoattractant protein-2 (MCP-2). Therefore, even if the above-mentioned chemokines are referred to as another names, it is natural that such chemokines are involved in the chemokine of the present invention. Further, it is needless to say that the chemokine of the present invention includes a substance being newly found in future and recognized to be in the category of the definition of the chemokine.

In the present invention, the adsorbent for removing a chemokine except interleukin-8 is characterized in that the adsorbent comprises a solid material having an anionic functional group.

The term "anionic functional group" in the present invention means a functional group which is negatively charged at a pH of neutral. The representative examples of such functional group are, for instance, carboxy group, sulfonic acid group, sulfonic group, sulfuric ester group, silanol group, phosphoric ester group, phenolic hydroxyl group and the like. However, the anionic functional group is not limited thereto.

The term "solid material" in the present invention means a material which is solid at ordinary temperature under ordinary pressure and water-insoluble.

Though the examples of the form of the solid material of the present invention are, for instance, a particle, a board, a film, a fiber, a hollow fiber and the like, the form is not limited thereto. In case where the solid material, with which a column is charged, is used; it should be the one wherein openings can be made which are enough for cells contained in body fluid to pass through them. For example, if the solid material is in the form of a particle, it is preferable that the average particle size is 5 to 1000 $\mu$m. Preferably, the average particle size is 25 to 1000 $\mu$m and most preferably, the average particle size is 50 to 600 $\mu$m. Among them, for reason that no increase of pressure loss occurs, it is preferable that the distribution of the particle size is narrow. Also, if the body fluid is blood, it is preferable that the average particle size is at least 200 $\mu$m.

And, if the solid material is in the form of a fiber and is hollow, it is preferable that the inner diameter is at least 1 $\mu$m. Preferably, the inner diameter is 2 to 500 $\mu$m and most preferably 5 to 200 $\mu$m. If the inner diameter is less than 1 $\mu$m, cells contained in body fluid may not be able to fully pass through the solid material.

Further, it is preferable that the solid material in the present invention has many pores of adequate size, namely the solid material has porous structure. The term "solid material having porous structure" in the present invention includes the followings: (1) a solid material comprising globular particles each formed by agglomeration of microglobular particles of a macromolecular material and which has spaces (macropores) formed between the agglomerated microglobular particles; (2) a solid material comprising the globular particles wherein each microglobular particle contains pores; and (3) a solid material comprising a copolymer having three dimensional network structure which contains pores (micropores) formed in a swollen state in an organic solvent having affinity with the copolymer.

And it is preferable that the surface of the solid material is smooth. It is not preferable that the surface of the solid material is rough, because non-specific adsorption of blood components is increased when body fluid containing a hemocyte passes through the solid material. Therefore, for example, the solid material may be coated with an adequate macromolecule such as a polymer of hydroxyethylmethacrylate.

There are various methods to obtain a solid material having an anionic functional group, which is an adsorbent of the present invention, and the solid material can be obtained by any methods. As the representative method, there can be exemplified, (1) a method for forming a solid material having an anionic functional group by means of polymerization or copolymerization using as a monomer or a crosslinking agent a compound having an anionic functional group or a functional group which can easily convert to the anionic functional group, and (2) a method for immobilizing a compound having an anionic functional group onto a solid material.

As the representative example of the monomer having an anionic functional group used in the method (1), there can be exemplified acrylic acid, methacrylic acid, styrenesulfonic acid and the like. The monomer is, however, not limited to these compounds.

Also, as the representative example of the monomer having a functional group which can easily convert to an anionic functional group, there can be exemplified an ester of acrylic acid, an ester of methacrylic acid and the like. The functional group in these monomers can easily convert to an anionic functional group by a reaction such as alkaline saponification. The monomer is, however, not limited to these representative examples.

And a solid material having an anionic functional group can be obtained by polymerization using such a representative monomer having an anionic functional group or by copolymerization using two or more kinds of these representative monomers.

Also, a solid material having an anionic functional group can be obtained by copolymerizing the above representative monomer having an anionic functional group with a monovinylmonomer represented by styrene, chlorostyrene and the like, further, with a polyvinylmonomer as a crosslinking agent, represented by divinylbenzene and trivinylbenzene.

As the method of (2), namely the method for immobilizing a compound having an anionic functional group onto a solid material, there can be exemplified a method for directly introducing an anionic functional group itself into a solid material, and a method for introducing a compound having an anionic functional group and a part other than the anionic functional group in its molecule into a solid material.

As the representative example of the method for directly introducing an anionic functional group itself into a solid material, there can be exemplified a method for directly introducing sulfuric ester group and/or sulfonic acid group into a solid material by reacting the solid material with a reagent such as chlorosulfonic acid or concentrated sulfuric acid. The method is, however, not limited to such a representative example.

In case where a compound having an anionic functional group and a part other than the anionic functional group in its molecule is introduced into a solid material, various methods which are widely known can be used without particular limitation. Since it is important that the compound having an anionic functional group is not released for preservation and safety of the adsorbent, the method by means of covalent bond capable of a strong immobilizing is preferable.

In this case, the compound having an anionic functional group in the present invention and a functional group available for the immobilization other than the anionic functional group is preferable.

As the representative example of the functional group available for immobilization, there can be exemplified amino group, amide group, carboxyl group, acid anhydride group, succinimide group, hydroxyl group, thiol group, aldehyde group, a halogen group, epoxy group, silanol group, tresyl group and the like. The functional group available for immobilization is, however, not limited to these groups.

As the representative example of the compound having an anionic functional group and a functional group other than the anionic functional group in its molecule, there can be exemplified a partially sulfuric ester compound derived from a polyolic compound such as diols, triols, saccharides or polysaccharides, and the like. These compounds are preferably used, since they have both of an anionic functional group and a functional group available for the immobilization.

Also, in this case, it is preferable that the compound having an anionic functional group, which is used for the immobilization, is a polyanionic compound having plural anionic functional groups in its molecule. Among the compounds, a polyanionic compound having a molecular weight of at least 1000, particularly at least 3000, is more preferable, since such a compound can easily introduce many anionic functional groups into a solid material and has high affinity for a chemokine. Though an upper limit of molecular weight of the polyanionic compound is not particularly limited, the upper limit is preferably $10^6$ in practical use. Also, the polyanionic compound may have one or more kinds of an anionic functional group.

The representative examples of the polyanionic compound are, for instance, synthetic polyanionic compounds such as poly(acrylic acid), poly(vinyl sulfuric acid), poly (vinyl sulfonic acid), poly(styrenesulfonic acid), poly (glutamic acid), poly(aspartic acid), poly(methacrylic acid), poly(phosphoric acid) and styrene-maleic acid copolymer; synthetic acidic polysaccharides such as dextran sulfate and carboxymethyl cellulose; acidic mucopolysaccharides which are derived from an organism and have sulfuric ester group, such as chondroitin sulfate, dermatan sulfate and keratan sulfate; acidic mucopolysaccharides which are derived from an organism and have N-sulfonic acid group and sulfuric ester group, such as heparin and heparan sulfate; polysaccharides which are derived from an organism and have an anionic functional group, such as chondroitin and phosphomannan; and nucleic acids which are derived from an organism, such as deoxyribonucleic acid and ribonucleic acid, but the polyanionic compound is not limited to the representative examples.

Among these representative compounds, use of a synthetic compound is more practical than use of a compound which is derived from an organism as it is, on the grounds that the synthetic compound having a high degree of purity can be obtained at a low price and that an amount of an introduced anionic functional group into a solid material can be controlled. Therefore, synthetic polyanionic compounds such as poly(acrylic acid), poly(vinyl sulfuric acid), poly (vinyl sulfonic acid), poly(styrenesulfonic acid), poly (glutamic acid), poly(aspartic acid), poly(methacrylic acid), poly(phosphoric acid) and a styrene-maleic acid copolymer, and synthetic acidic polysaccharides such as dextran sulfate and carboxymethyl cellulose, are preferably used.

Further, in case of immobilizing the polyanionic compound onto a solid material, one or more kinds of the polyanionic compound may be used.

Also, as the solid material in this case, it is preferable that the solid material has a functional group available for bonding to the compound having an anionic functional group. The representative examples of the functional group are, for instance, amino group, amido group, carboxyl group, acid anhydride group, succinimide group, hydroxyl group, thiol group, aldehyde group, a halogen group, epoxy group, silanol group and tresyl group, but the functional group is not limited to them.

The representative examples of the solid material having such a functional group are, for instance, inorganic solid materials such as glass and silica gel; solid materials comprising polysaccharides such as cellulose, chitin, chitosan, agarose, dextran and derivatives thereof; and synthetic high polymers such as poly(vinyl alcohol), polyacrylamide, poly (acrylic acid), poly(methacrylic acid), derivatives thereof and copolymers thereof, but the solid material is not limited to them. Further, these solid materials may be activated by a method such as cyanogen halide method, epichlorohydrin method, bisepoxide method or bromoacetylbromide method.

It is preferable that the adsorbent in the present invention comprises a solid material having a proper amount of an anionic functional group. If the amount of the anionic functional group is too small, there is no effect of the anionic functional group. If the amount is too large, non-specific adsorption occurs. Therefore, it is necessary that the adsorbent in the present invention has 100 nmol to 10 mmol of the anionic functional group per unit volume (1 ml) of the solid material which swells in water. Preferably, the adsorbent has 1 μmol to 5 mmol, most preferably 5 μmol to 3 mmol of the anionic functional group per unit volume (1 ml) of the solid material which swells in water.

Among the above-mentioned solid materials having an anionic functional group, a solid material comprising styrene-divinylbenzene copolymer having a sulfonic acid group, is preferable. Such a styrene-divinylbenzene copolymer having a sulfonic acid group is generally used as a strongly acidic cation-exchange resin.

There are various copolymerization methods to obtain the above-mentioned styrene-divinylbenzene copolymer, and copolymerization can be carried out by any methods. As the representative method, there can be exemplified, for instance, a method wherein a proper amount of divinylbenzene is added to styrene, and a polymerization catalyst, for instance, a small amount of benzoyl peroxide and water, are added to the mixture, and a suspending agent such as bentonite or alginic acid is added thereto, and then the obtained mixture is intensively agitated to carry out polymerization.

As the method for introducing a sulfonic acid group into the above-mentioned styrene-divinylbenzene copolymer, there are various methods, for instance, a method wherein the above-mentioned copolymer is treated with concentrated sulfuric acid or chlorosulfonic acid and the like, but the method is not limited thereto.

The amount of a sulfonic acid group which is introduced into a styrene-divinylbenzene copolymer, can be represented by ion-exchange capacity. In order to adsorb a chemokine, it is necessary that a sulfonic acid group is introduced into a styrene-divinylbenzene copolymer at a proper density. Preferably, the ion-exchange capacity of the above-mentioned styrene-divinylbenzene copolymer having a sulfonic acid group is 0.01 to 5 meq/ml, more preferably 0.1 to 2 meq/ml. If the capacity is less than 0.01 meq/ml, major proteins in body fluid (mainly albumin) are non-specifically adsorbed. If the capacity is more than 5 meq/ml, manufacture of an adsorbent maintaining ability to adsorb a chemokine becomes difficult.

In order to adsorb more chemokine, it is preferable that the above-mentioned adsorbent which comprises a styrene-divinylbenzene copolymer having a sulfonic acid group, has pores of a size sufficient to enable a chemokine to enter them. The pores have a pore distribution, and the pore distribution thereof can be measured by mercury porosimetry method or nitrogen adsorption method. In order to adsorb a chemokine, the pores of the styrene-divinylbenzene copolymer having a sulfonic acid group have preferably 50 to 2000 Å of the main pore distribution, more preferably 100 to 1000 Å of the main pore distribution.

In order to adsorb more chemokine, it is preferable that an adsorbent which comprises a styrene-divinylbenzene copolymer having a sulfonic acid group, has large surface area available for adsorption per unit quantity of the adsorbent (specific surface area). Preferably, specific surface area of the adsorbent is at least 10 m$^2$/g, more preferably at least 50 m$^2$/g.

There are various methods, as a method for adsorbing and removing a chemokine from body fluid, using the adsorbent according to the present invention. As the representative method, there are exemplified a method wherein body fluid is taken and stored in a bag or the like, and the adsorbent is mixed therewith to adsorb and remove a chemokine, and then the adsorbent is filtered off to obtain body fluid from which the chemokine is removed, and a method wherein a vessel having an inlet and an outlet for body fluid is equipped with a filter through which body fluid can pass and the adsorbent cannot pass, and the vessel is charged with the adsorbent, and body fluid is flowed. Any methods can be used. With respect to the latter method, however, the operation thereof is simple, and a chemokine can be removed efficiently on-line from body fluid, especially blood of a patient by incorporating the latter method into extracorporeal circulation cycle. Therefore, the adsorbent of the present invention is suitable for this method.

In the extracorporeal circulation cycle described herein, the adsorbent of the present invention can be used alone or in combination with the other extracorporeal circulation treatment system. As an example of the combination, there is a combination with artificial dialysis cycle, and then, the combination can also be used for hemodialysis therapy.

An adsorber for removing a chemokine of the present invention with the adsorbent for removing a chemokine is more specifically explained referring to FIG. 1 which is schematic cross section of an Example.

In FIG. 1, 1 represents an inlet for body fluid; 2 represents an outlet for body fluid; 3 represents an adsorbent for removing a chemokine of the present invention; 4 and 5 represent a filter for preventing the adsorbent from flowing out, thereby body fluid and a component contained in body fluid can pass but the adsorbent for removing a chemokine cannot pass; 6 represents a column and 7 represents an adsorber for removing a chemokine. However, the adsorber for removing a chemokine is not limited to such a representative example, any adsorber wherein a vessel which has an inlet and an outlet for body fluid and is equipped with a means to prevent the adsorbent for removing a chemokine from flowing to the outside of the vessel, is charged with the above-mentioned adsorbent, can be available.

As the above-mentioned means to prevent the adsorbent from flowing out, there can be exemplified, for instance, mesh, non woven fabric, cotton plug and the like. Also, a shape, material and size of the vessel of the above-mentioned adsorber are not particularly limited. As a preferable example, there is a cylindrical column with about 150 to about 400 ml of capacity and about 4 to about 10 cm of diameter.

The present invention is explained in detail by means of the following Examples and, however, the present invention is not limited to the following Examples. Also, in the following Examples, as a chemokine to be adsorbed, there can be exemplified MIP-1α which has less than 7 of the isoelectric point (the isoelectric point: 4.7) and is classified into CC subfamily. However, it is needless to say that, in the same manner as MIP-1α, a chemokine other than MIP-1α can be applied for the present invention.

EXAMPLE 1

To 10 ml of CK gel A-3 which was a cellulose carrier (particle size: 45–105 μm, made by CHISSO CORPORATION, hereinafter referred to as CKA-3), 4 g of a 20% (w/v) aqueous solution of sodium hydroxide, 12 g of heptane and one drop of a nonion-type surfactant Tween 20 (made by Bio-Rad Laboratories, Inc.) were added. After agitating for 2 hours at 40° C., 5 g of epichlorohydrin was added thereto and agitated for 2 hours. Then, the obtained gel was washed with water and filtrated to obtain an epoxidated CKA-3. The amount of the introduced epoxy group was 30 μmol per ml of unit volume of the epoxidated CKA-3 which swelled in water. To 2 ml of the obtained epoxidated CKA-3, 0.12 g of sodium dextran sulfate of which the limiting viscosity number was 0.027 dl/g and the sulfur content was 17.7% by weight (molecular weight: approximately 4000), and 2 ml of water were added (the concentration of sodium dextran sulfate was approximately 2.5%

(w/v)). And, the obtained admixture was adjusted to pH 11 and shaked for 16 hours at 45° C. After that, the gel was filtered off and was washed with a 2M aqueous solution of sodium chloride, a 0.5M solution of sodium chloride and water in this turn to obtain the CKA-3 on which sodium dextran sulfate was immobilized (hereinafter referred to as C-1). The amount of the anionic functional group per unit volume of the adsorbent which swelled in water (1 ml) was 12 μmol.

Then 0.5 ml of C-1 was weighed out as sedimentation volume and thereto was added 3 ml of human MIP-1α addition human serum which is prepared by adding recombinant human MIP-1α (made by R & D systems) to human serum (the concentration of MIP-1α: 1.2 ng/ml). Then the obtained admixture was shaked for 2 hours at 37° C. to adsorb human MIP-1α. The concentration of MIP-1α in supernatant was measured by means of a measurement kit for human MIP-1α made by R & D systems.

Result

| Adsorbent | Concentration of MIP-1α in supernatant (ng/ml) |
|---|---|
| C-1 | 0.49 |

Comparative Example 1

As sedimentation volume, 0.5 ml of CKA-3 was weighed out and thereto was added 3 ml of human MIP-1α addition human serum which was prepared in the same way as in Example 1. And then, the adsorption experiment was carried out, and the concentration of MIP-1α in supernatant was measured in the same way as in Example 1.

Result

| Adsorbent | Concentration of MIP-1α in supernatant (ng/ml) |
|---|---|
| CKA-3 | 1.1 |

It is found that, contrary to Comparative Example 1, the concentration of MIP-1α in Example 1 was extremely decreased, and MIP-1α in a solution can be efficiently adsorbed and removed by means of the adsorbent which was prepared by introducing an anionic functional group into a cellulose carrier.

EXAMPLE 2

As sedimentation volume, 0.5 ml of AMBERLITE IRC-50 which was a cation-exchange resin having a carboxyl group (the amount of the anionic functional group per unit volume of the adsorbent which swelled in water (1 ml): 3 mmol) (made by Rohm & Hass Co.) was weighed out, and thereto was added 3 ml of human MIP-1α addition human serum which was prepared in the same way as in Example 1. And then, the adsorption experiment was carried out and the concentration of MIP-1α in supernatant was measured in the same way as in Example 1.

Result

| Adsorbent | Concentration of MIP-1α in supernatant (ng/ml) |
|---|---|
| AMBERLITE IRC-50 | 0.44 |

Comparative Example 2

As sedimentation volume, 0.5 ml of AMBERLITE IRA-938 which was an anion-exchange resin having a quaternary ammonium group (made by Rohm & Haas Co.) was weighed out, and thereto was added 3 ml of human MIP-1α addition human serum which was prepared in the same way as in Example 1. And then, the adsorption experiment was carried out and the concentration of MIP-1α in supernatant was measured in the same way as in Example 1.

Result

| Adsorbent | Concentration of MIP-1α in supernatant (ng/ml) |
|---|---|
| AMBERLITE IRC-938 | 1.0 |

Comparative Example 3

As sedimentation volume, 0.5 ml of DEAE-TOYOPEARL 650 which was an anion-exchange resin having a diethylaminoethyl group (made by TOSOH Corporation) was weighed out, and thereto was added 3 ml of human MIP-1α addition human serum which was prepared in the same way as in Example 1. And then, the adsorption experiment was carried out and the concentration of MIP-1α in supernatant was measured in the same way as in Example 1.

Result

| Adsorbent | Concentration of MIP-1α in supernatant (ng/ml) |
|---|---|
| DEAE-TOYOPEARL 650 | 1.0 |

It is found that, contrary to Comparative Examples 2 and 3 wherein the anion-exchange resin having the cationic functional group was used, the concentration of MIP-1α in supernatant in Example 2 wherein the cation-exchange resin having the anionic functional group was used, was extremely decreased, and MIP-1α can be efficiently adsorbed and removed using an adsorbent having an anionic functional group, regardless of an isoelectric point of a chemokine.

EXAMPLE 3

DIAION HPK-55H which was a strongly acidic cation-exchange resin, made by MITSUBISHI KASEI CORPORATION and a styrene-divinylbenzene copolymer having a sulfonic acid group (the ion-exchange capacity: approximately 1 meq/ml) was converted into Na type, and then was equilibrated with physiological saline. In a test tube, 0.5 ml of the obtained resin was placed, and excess physiological saline was removed. Thereto, 3 ml of human MIP-1α addition human serum which was prepared by adding recombinant human MIP-1α (made by R & D systems) to human serum (the concentration of MIP-1α: 1.1 ng/ml, the concentration of albumin: 4.0 g/dl) was added and shaked for 2 hours at 37° C. The concentration of MIP-1α in supernatant was measured in the same way as in Example 1. Also, the concentration of albumin was measured by Bromocresol Green method (BCG method).

Comparative Example 4

In a test tube, 0.5 ml of physiological saline was placed, and thereto was added 3 ml of human MIP-1α addition human serum which was used in Example 3 (the concentration of MIP-1α: 1.1 ng/ml, the concentration of albumin: 4.0 g/dl) was added and shaked for 2 hours at 37° C. Each concentration of MIP-1α and albumin in supernatant was measured in the same way as in Example 3.

| | Result | |
|---|---|---|
| No. of Ex. or Com. Ex. (Adsorbent) | Concentration of MIP-1α in supernatant (ng/ml) | Concentration of albumin in supernatant (g/dl) |
| Ex. 3 (DIAION HPK-55H) | 0.02 | 3.5 |
| Com. Ex. 4 (None) | 0.9 | 3.4 |

It is found that, contrary to Comparative Example 4, the concentration of MIP-1α in Example 3 was extremely decreased, and MIP-1α in a solution can be efficiently adsorbed and removed by means of the above-mentioned strongly acidic cation-exchange resin.

Comparative Example 5

DIAION HP-20 made by MITSUBISHI KASEI CORPORATION, comprising a styrene-divinylbenzene copolymer and having no sulfonic acid group, was equilibrated with physiological saline. In a test tube, 0.5 ml of the obtained resin was placed, and thereto was added 3 ml of human MIP-1α addition human serum which was used in Example 3 (the concentration of MIP-1α: 1.1 ng/ml, the concentration of albumin: 4.0 g/dl) and shaked for 2 hours at 37° C. Each concentration of MIP-1α and albumin in supernatant was measured in the same way as in Example 3.

| | Result | |
|---|---|---|
| No. of Com. Ex. (Adsorbent) | Concentration of MIP-1α in supernatant (ng/ml) | Concentration of albumin in supernatant (g/dl) |
| Com. Ex. 5 (DIAION HP-20) | 0.02 | 3.1 |

It is found that, in Comparative Example 5, the concentration of albumin in supernatant was extremely decreased, and albumin was extremely adsorbed in case of using the styrene-divinylbenzene copolymer to which no sulfonic acid group was introduced.

EXAMPLE 4

AMBERLITE 200C which was a strongly acidic cation-exchange resin, made by Rohm & Haas Co. and a styrene-divinylbenzene copolymer having a sulfonic acid group (the ion-exchange capacity: approximately 1.75 meq/ml) was equilibrated with physiological saline. In a test tube, 0.5 ml of the obtained resin was placed, and thereto was added 3 ml of human MIP-1α addition human serum which was used in Example 3 (the concentration of MIP-1α: 1.1 ng/ml, the concentration of albumin: 4.0 g/dl) and shaked for 2 hours at 37° C. Each concentration of MIP-1α and albumin in supernatant was measured in the same way as in Example 3.

| | Result | |
|---|---|---|
| No. of Ex. (Adsorbent) | Concentration of MIP-1α in supernatant (ng/ml) | Concentration of albumin in supernatant (g/dl) |
| Ex. 4 (AMBERLITE 200C) | 0.03 | 3.7 |

It is found that, in the same manner as in Example 3, the concentration of MIP-1α was extremely decreased, and MIP-1α in a solution can be efficiently adsorbed and removed by means of the above-mentioned strongly acidic cation-exchange resin.

In addition to the ingredients used in the Examples, other ingredients can be used in the Examples as set forth in the specification to obtain substantially the same results.

What we claim is:

1. A method for removing a chemokine, which comprises bringing an adsorbent comprising a styrene-divinylbenzene copolymer having a sulfonic acid group into contact with body fluid containing the chemokine.

2. The method of claim 1, wherein ion-exchange capacity of the styrene-divinylbenzene copolymer having a sulfonic acid group is from 0.01 meq/ml to 5 meq/ml.

3. The method of claim 1, wherein a vessel which has an inlet and an outlet for fluid contains the adsorbent for removing a chemokine in the vessel.

4. The method of claim 1, wherein the chemokine is a chemokine other than interleukin-8.

* * * * *